(12) United States Patent
Ledoux et al.

(10) Patent No.: US 7,569,738 B2
(45) Date of Patent: Aug. 4, 2009

(54) METHOD AND APPARATUS FOR ADDITION OF AQUEOUS SOLUTIONS TO HIGH TEMPERATURE PROCESSES

(75) Inventors: Marcus Ledoux, Baton Rouge, LA (US); Jim Butler, League City, TX (US); Jim Merrill, Katy, TX (US); Clint Persick, Denham Springs, LA (US); Ashley Rabalais, Prairieville, LA (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 12/238,552

(22) Filed: Sep. 26, 2008

(65) Prior Publication Data

US 2009/0054715 A1    Feb. 26, 2009

Related U.S. Application Data

(62) Division of application No. 11/058,849, filed on Feb. 15, 2005, now abandoned.

(51) Int. Cl.
*C07C 5/333*    (2006.01)

(52) U.S. Cl. ..................................... 585/444; 585/440
(58) Field of Classification Search ................. 585/440, 585/444
See application file for complete search history.

(56) References Cited

U.S. PATENT DOCUMENTS 5,739,071 A * 4/1998 Chen et al. ..................... 502/53

* cited by examiner

*Primary Examiner*—Thuan Dinh Dang
(74) *Attorney, Agent, or Firm*—Tenley R. Krueger

(57) ABSTRACT

Methods and systems for extending the life of a dehydrogenation catalyst are described herein. For example, one embodiment includes providing a reaction vessel loaded with a dehydrogenation catalyst with a feedstream via a conduit in operable communication with the reaction vessel. The feedstream may include an alkyl aromatic hydrocarbon and the dehydrogenation catalyst may be adapted to convert the alkyl aromatic hydrocarbon to a vinyl aromatic hydrocarbon. The feedstream may be contacted with an aqueous catalyst life extender, wherein the aqueous catalyst life extender enters the conduit at a linear velocity sufficient to prevent vaporization of the catalyst life extender in the conduit prior to contact with the feedstream.

6 Claims, 4 Drawing Sheets

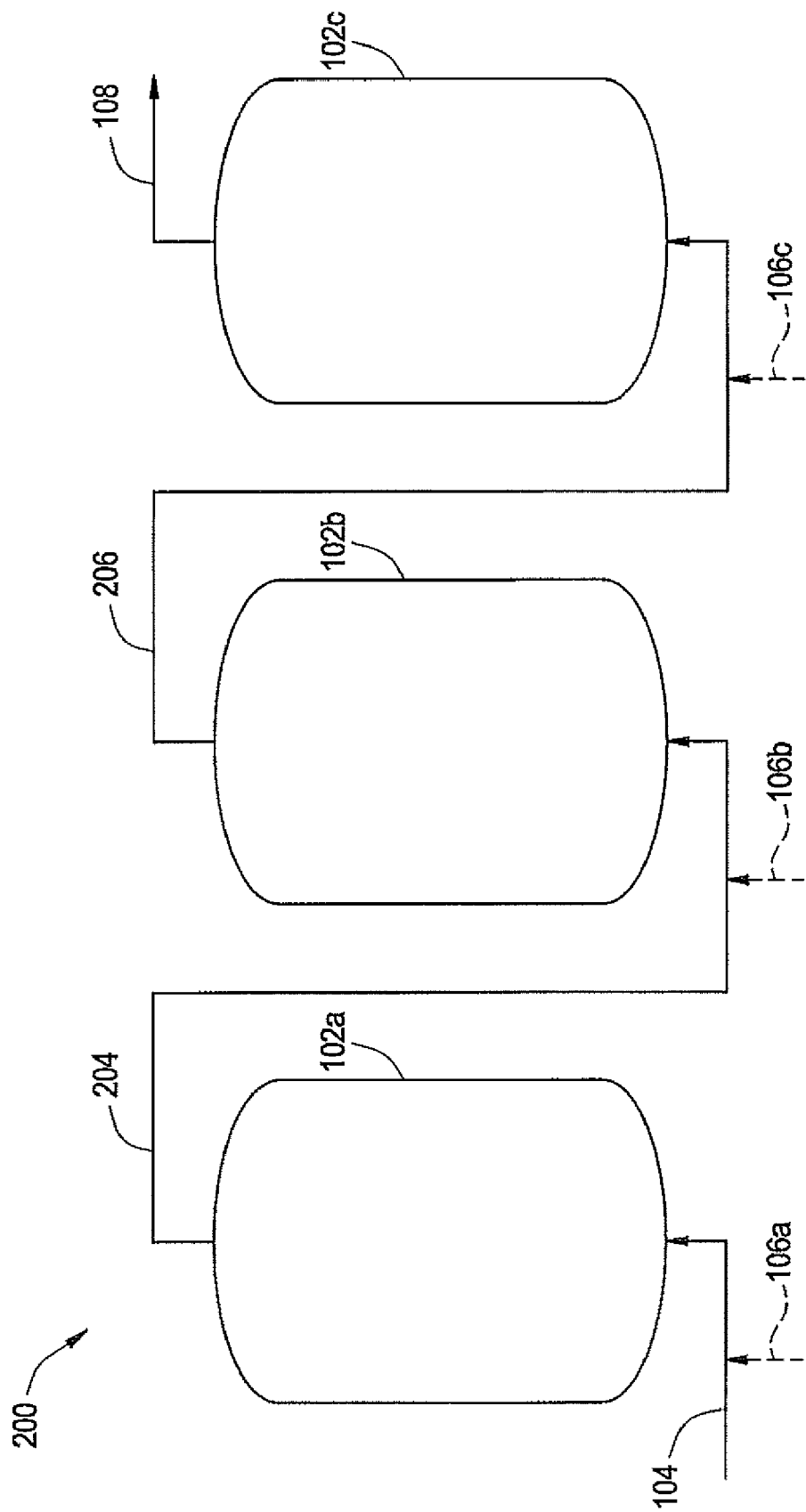

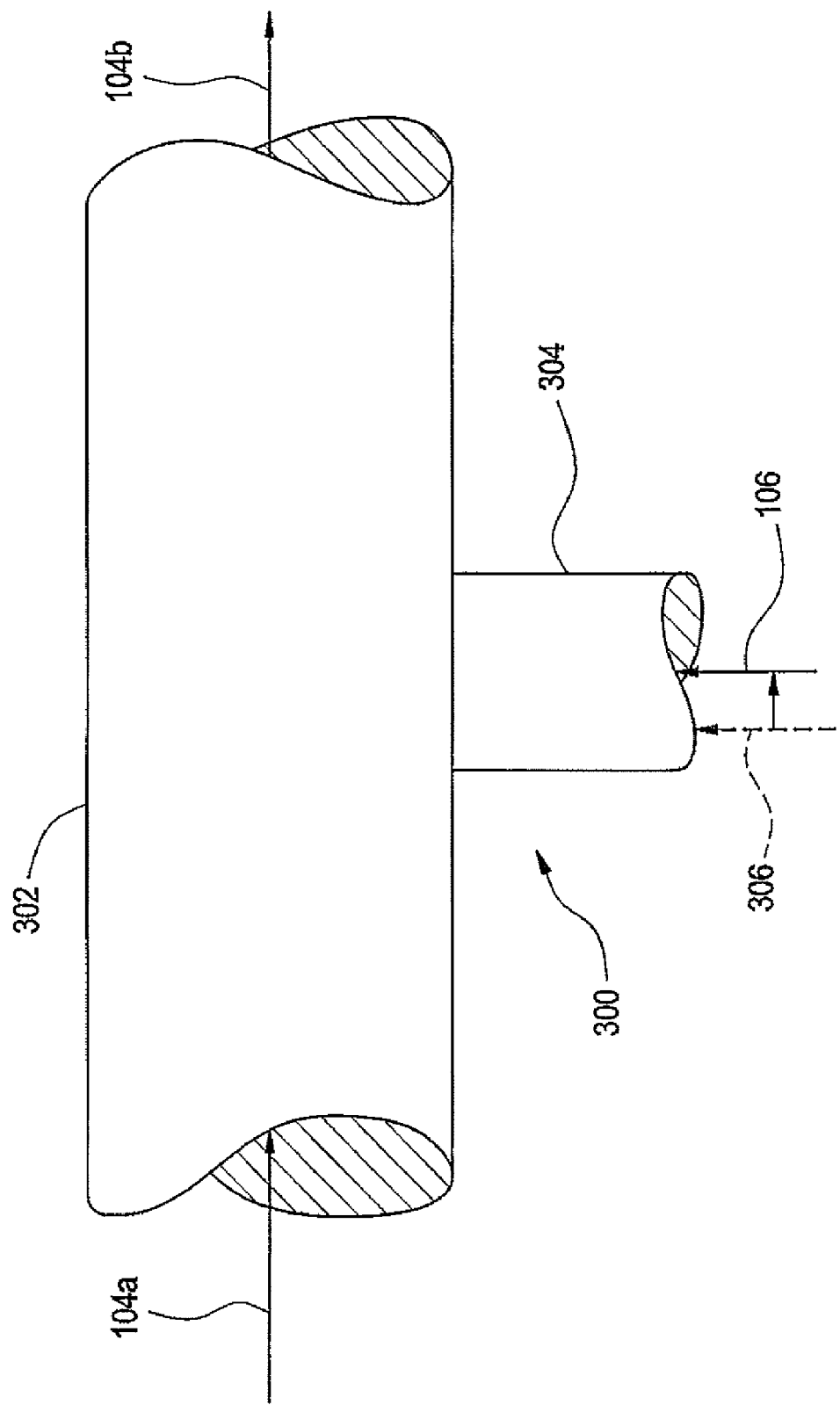

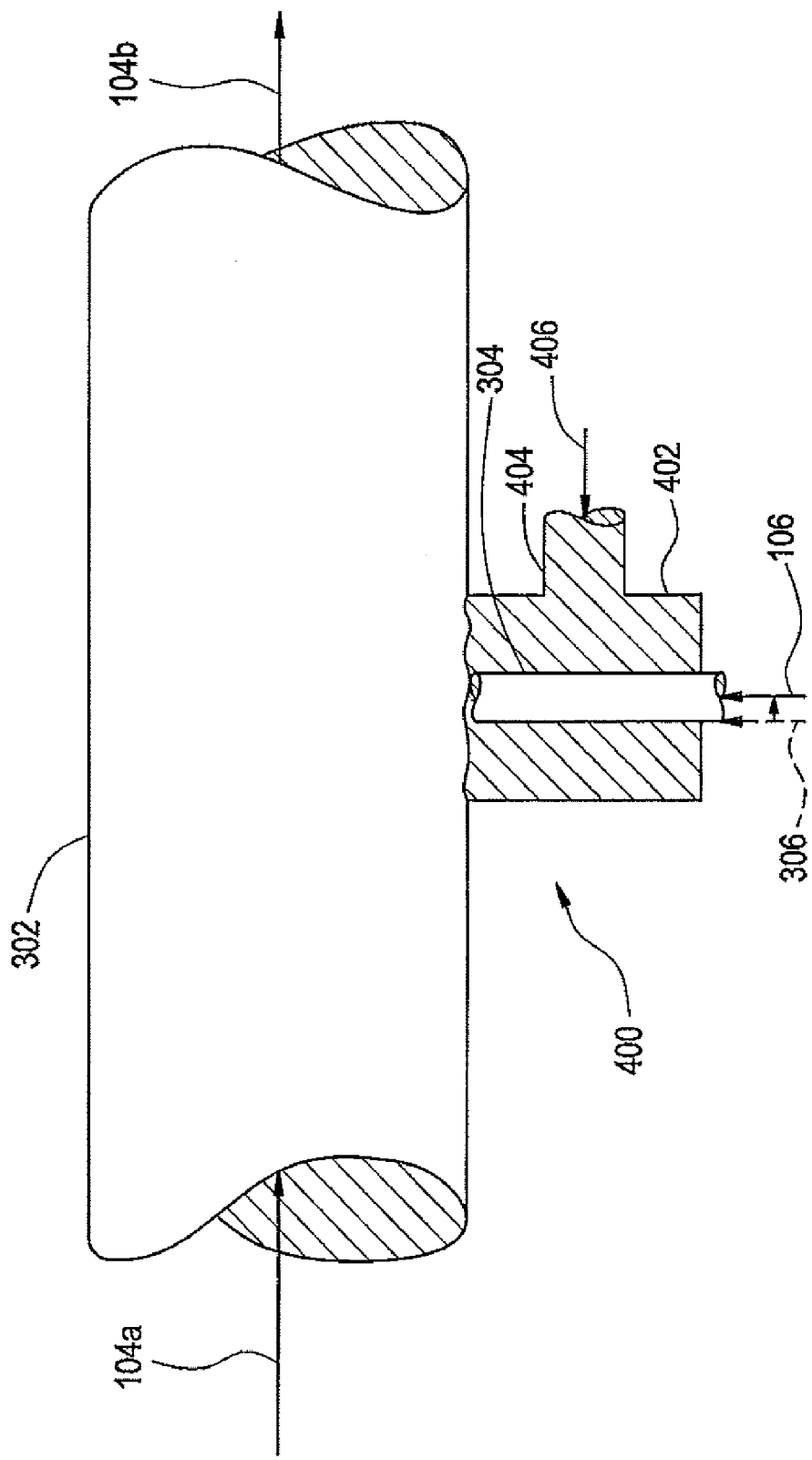

METHOD AND APPARATUS FOR ADDITION OF AQUEOUS SOLUTIONS TO HIGH TEMPERATURE PROCESSES

FIELD

Embodiments of the present invention generally relate to aqueous salt addition to high temperature processes.

BACKGROUND

Catalytic dehydrogenation processes generally include the conversion of a paraffin alkylaromatic to the corresponding olefin in the presence of a dehydrogenation catalyst. During such dehydrogenation processes, it is desirable to maintain both high levels of conversion and high levels of selectivity. Unfortunately, dehydrogenation catalysts tend to lose activity when exposed to reaction environments, thereby reducing the level of conversion and/or the level of selectivity. Such losses may result in an undesirable loss of process efficiency. Various methods for catalyst regeneration exist, but such methods generally involve stopping the reaction process and in some cases, removing the catalyst for external regeneration, resulting in increased costs, such as costs related to heat loss and lost production.

One regeneration method includes the addition of a catalyst life extender to the dehydrogenation process. Such processes may avoid/delay the need for catalyst removal from the reaction vessel for regeneration and/or disposal. Unfortunately, such processes generally have required costly implementation systems to avoid system problems, such as fouling and plugging of the process lines.

Therefore, it is desirable to overcome catalyst degradation, while at the same time ensuring that such methods of overcoming the degradation do not result in costly implementation systems, fouling and/or plugging.

SUMMARY

Embodiments of the invention generally include a catalytic dehydrogenation system. In one embodiment, the catalytic dehydrogenation system generally includes at least one reaction vessel loaded with a dehydrogenation catalyst adapted to convert an alkyl aromatic hydrocarbon to a vinyl aromatic hydrocarbon, the reaction vessel including a vessel inlet and a vessel outlet and a first conduit operably connected to the vessel inlet and adapted to provide a feedstream thereto, the feedstream comprising the alkyl aromatic hydrocarbon. Such an embodiment further includes a supply system including a second conduit adapted to provide an aqueous catalyst life extender to the feedstream at a linear velocity sufficient to minimize fouling within the first conduit.

Another embodiment includes providing a reaction vessel loaded with a dehydrogenation catalyst with a feedstream. The feedstream is provided via a conduit in operable communication with the reaction vessel, the feedstream including an alkyl aromatic hydrocarbon and the dehydrogenation catalyst adapted to convert the alkyl aromatic hydrocarbon to a vinyl aromatic hydrocarbon. Such an embodiment also includes contacting the feedstream with an aqueous catalyst life extender, wherein the aqueous catalyst life extender enters the conduit at a linear velocity sufficient to prevent vaporization of the catalyst life extender in the conduit prior to contact with the feedstream.

Yet another embodiment includes at least one reaction vessel loaded with a dehydrogenation catalyst, the reaction vessel including a vessel inlet and a vessel outlet adapted to pass a feedstream therethrough to contact the dehydrogenation catalyst and form a product, a first conduit operably connected to the vessel inlet and adapted to provide the feedstream thereto and a supply system, the supply system including a second conduit adapted to provide an aqueous catalyst life extender to the feedstream at a linear velocity sufficient to minimize fouling within the first conduit.

BRIEF DESCRIPTION OF DRAWINGS

FIG. 2 illustrates a multistage catalytic dehydrogenation system.
FIG. 3 illustrates an embodiment of a supply system.
FIG. 4 illustrates an alternative embodiment of a supply system.

DETAILED DESCRIPTION

Introduction and Definitions

Figure 1:
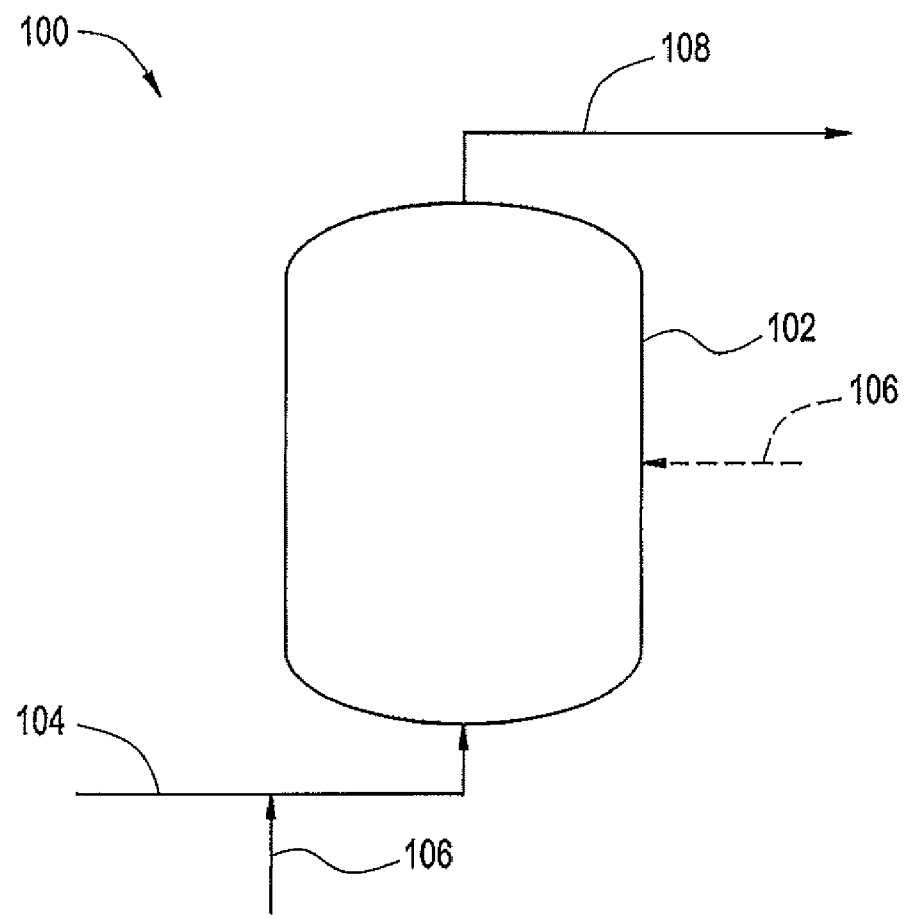
FIG. 1 illustrates a catalytic dehydrogenation system.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology. Various terms as used herein are shown below. To the extent a term used in a claim is not defined below, it should be given the broadest definition persons in the pertinent art have given that term as reflected in printed publications and issued patents at the time of filing.

As used herein, the term "conversion" means the percentage of paraffins or alkylaromatic hydrocarbon transformed.

The term "selectivity" means percentage of alkylaromatic hydrocarbon transformed to the desired product.

The term "activity" refers to the weight of product produced per weight of the catalyst used in the dehydrogenation process per hour of reaction at a standard set of conditions (e.g., grams product/gram catalyst/hr).

The term "loaded" refers to introduction of a catalyst within a reaction vessel.

As used herein, the term "alkali metal" includes but is not limited to, potassium, sodium, lithium and other members of the group IA and IIA metals of the periodic table, such as rubidium and cesium. In the conversion of ethylbenzene to styrene, the alkali metal is generally potassium, but depends upon the alkali metal present in the dehydrogenation catalyst.

As used herein, the term "regeneration" means a process for renewing catalyst activity and/or making the catalyst reusable after it's activity has reached an unacceptable level. Examples of such regeneration may include passing steam over the catalyst bed or burning off carbon residue.

Process

FIG. 1 illustrates a catalytic dehydrogenation system 100 including at least one reaction vessel 102 loaded with a dehydrogenation catalyst (not shown). An alkyl aromatic hydrocarbon (AAH) feedstream 104 enters the reaction vessel 102 and contacts the dehydrogenation catalyst to form a vinyl aromatic hydrocarbon (VAH) exit stream 108. Although the process is described here in terms of an alkyl aromatic hydrocarbon feedstream and a vinyl aromatic hydrocarbon exit stream, it is within embodiments of the invention described herein that the feedstream may be and/or include other compounds that may be contacted with a dehydrogenation catalyst to form a product, such as propane (converted to propylene) or butylene (converted to butadiene.) It is further contemplated that the embodiments described herein, such as the supply system described further below, may be used for high temperature processes not utilizing dehydrogenation catalysts, but in need of aqueous injection into the feedstream.

One example of a catalytic dehydrogenation process includes dehydrogenating alkyl aromatic hydrocarbons over a solid catalyst component in the presence of steam (not shown) to form the VAH. Generally, the steam contacts the AAH feedstream 104 prior to the AAH feedstream 104 entering the reaction vessel 102, but may be added to the system 100 in any manner known to one skilled in the art. Although the amount of steam contacting the AAH is determined by individual process parameters, the AAH feedstream 104 may have a steam to AAH weight of from about 0.01 to about 15:1, or from about 0.3:1 to about 10:1, or from about 0.6:1 to about 3:1, or from about 0.8:1 to about 2:1, for example.

One specific embodiment includes the conversion of ethylbenzene to styrene, where the VAH exit stream 108 may include styrene, toluene, benzene, and/or unreacted ethylbenzene, for example. In other embodiments, the process includes the conversion of ethyltoluene to vinyltoluene, cumene to alpha-methylstyrene and/or normal butylenes to butadiene, for example.

The dehydrogenation processes discussed herein are high temperature processes. As used herein, the term "high temperature" refers to process operation temperatures, such as reaction vessel and/or process line temperatures (e.g., the temperature of the feedstream at the vessel inlet) of from about 150° C. to about 1000° C., or from about 300° C. to about 800° C., or from about 500° C. to about 700° C., or from about 550° C. to about 650° C., for example.

A variety of catalysts can be used in the catalytic dehydrogenation system 100. A representative discussion of some of those catalysts (e.g., dehydrogenation catalysts) is included below, but is in no way limiting the catalysts that can be used in the embodiments described herein.

The dehydrogenation catalysts discussed herein generally include an iron compound and at least one alkali metal compound. For example, the dehydrogenation catalyst may include from about 40 weight percent to about 90 weight percent iron, or from about 70 wt. % to about 90 wt. % iron, or from about 80 wt. % to about 90 wt. % iron. The iron compound can be iron oxide, or another iron compound known to one skilled in the art.

Further, the dehydrogenation catalyst may include from about 5 weight percent to about 60 weight percent alkali metal compound, or from about 8 wt. % to about 30 wt. % alkali metal compound, for example. The alkali metal compound may be potassium oxide, potassium hydroxide, potassium acetate, potassium carbonate or another alkali metal compound known to one skilled in the art, for example.

Additionally, the dehydrogenation catalysts may further include additional catalysis promoters (e.g., up to about 20 wt. % measured as their oxides, or from about 1 wt. % to about 4 wt. %), such as nonoxidation catalytic compounds of Groups IA, IB, IIA, IIB, IIIA, VB, VIB, VIIB and VIII and rare earth metals, such as zinc oxide, magnesium oxide, chromium or copper salts, potassium oxide, potassium carbonate, oxides of chromium, manganese, aluminum, vanadium, magnesium, thorium and/or molybdenum, for example.

Such dehydrogenation catalysts are well known in the art and some of those that are available commercially include: the S6-20, S6-21 and S6-30 series from BASF Corporation; the C-105, C-015, C-025, C-035, and the FLEXICAT series from CRI Catalyst Company, L.P.; and the G-64, G-84 and STYROMAX series from Sud Chemie, Inc. Dehydrogenation catalysts are further described in U.S. Pat. Nos. 5,503,163 (Chu); U.S. Pat. No. 5,689,023 (Hamilton, Jr.) and U.S. Pat. No. 6,184,174 (Rubini, el al.), which are incorporated by reference herein.

The dehydrogenation catalyst may be loaded into any reaction vessel 102 known to one skilled in the art for the conversion of an AAH to a VAH. For example, the reaction vessel 102 may be a fixed bed vessel, a fluidized bed vessel and/or a tubular reactor.

Although a single stage process is shown in FIG. 1, multistage processes are often utilized to form vinyl aromatic hydrocarbons and an example of such (three stages 200) is shown in FIG. 2. Although FIG. 2 illustrates three reactors/stages, any number or combination of reactors may be utilized. In a multistage process, such as process 200, the exit stream (204, 206) of one reaction vessel (102A, 102B) becomes the feedstream (204, 206) to another reaction vessel (102B, 102C). Therefore, when the dehydrogenation process is a multistage process, the term "feedstream" as used herein, may be the exit stream from a previous reactor, a "fresh" feedstream and/or a recycled stream, for example. In such embodiments, the feedstream (e.g., 204, 206) may include steam, partially reacted alkyl aromatic hydrocarbon, unreacted alkyl aromatic hydrocarbon and/or vinyl aromatic hydrocarbon, for example. Further, it is known in the art that additional process equipment, such as reheaters (not shown) may be included to maintain and/or restore process stream temperatures within a desired range, such as within a high temperature range at a reaction vessel inlet.

One process for preparing vinyl aromatic hydrocarbons is the "Dow Process", which supplies superheated steam (720° C.) to a vertically mounted fixed bed catalytic reactor. The steam is generally injected into the reactor in the presence of a vaporized feedstream. See, The Chemical Engineers Resource Page at www.cheresources.com/polystymonzz.shtml.

Catalyst Life Extender

During such dehydrogenation processes, it is desirable to maintain both high levels of conversion and high levels of selectivity. Unfortunately, catalysts tend to lose activity when exposed to reaction environments, thereby reducing the level of conversion and/or the level of selectivity. Such losses may result in an undesirable loss of process efficiency. Various methods for catalyst regeneration exist, but such methods generally involve stopping the reaction process and in some cases, removing the catalyst for external regeneration, resulting in increased costs, such as costs related to heat loss and lost production.

One method for overcoming the loss of catalyst activity includes raising the temperature of the feedstream and/or the reaction vessel. Such temperature increases raise the rate of reaction in order to offset the continuing loss of catalyst activity. The embodiments described herein contemplate such temperature increases in combination with other processes for catalyst regeneration. Unfortunately, above a certain temperature, the mechanical temperature limit of the process equipment or the dehydrogenation catalyst may be reached, thereby increasing the potential degradation of the catalyst physical structure and/or the integrity of the process equipment.

Returning to FIG. 1, one regeneration method that is described further below includes the addition of a catalyst life extender (CLE) 106 to the dehydrogenation process 100. The CLE 106 may be added to the system 100 at various points, including the reaction vessel 102, the catalyst bed (not shown) and/or process stream 104, for example. Such processes may avoid/delay the need for catalyst removal from the reaction vessel 102 for regeneration and/or disposal.

The catalyst life extender 106 may be selected from non-halogen sources of alkali metal ions and may include a combination thereof. The amount of catalyst life extender 106 added to the process depends at least in part on the reaction conditions, equipment, feedstream composition and/or the catalyst life extender 106 being used, for example.

Unfortunately, such an addition method may result in costly addition methods, such as the vaporization of molten potassium in order to eliminate and/or reduce fouling. For example, in the initial phases of industry implementation, aqueous potassium hydroxide (KOH) addition was attempted. It was determined that KOH addition, with the KOH being at ambient temperature, resulted in severe reactor fouling and plugging of the injection hardware and/or process line. Therefore, such catalyst life extenders are generally preheated to a temperature similar to that of the feedstream prior to addition.

However, in one embodiment, the catalyst life extender 106 is a compound containing potassium, is neither excessively deliquescent nor dangerously reactive and has a melting point or vapor point such that it can be used at dehydrogenation process temperatures without blocking process lines or fouling process equipment. For example, the catalyst life extender 106 may be a potassium salt of a carboxylic acid, such as potassium acetate.

Unexpectedly, it has been found that such catalyst life extenders (in aqueous form) are capable of being injected into high temperature process lines without the expected plugging/fouling. Rather, aqueous addition of the carboxylic acids described above resulted in markedly decreased fouling and in some instances, no fouling for extended periods of time. Previous attempts at aqueous potassium hydroxide addition resulted in plugging/fouling after only a short period of time, such as days, versus weeks or months.

Further, the catalyst life extender 106 is generally substantially free of any catalysts poisons. For example, it has been reported that halogen ions, such as chloride, may poison dehydrogenation catalysts. Therefore, the catalyst life extender 106 includes little or no halogen substituents.

The catalyst life extender 106 may be supplied to the system 100 at a rate equivalent to a continuous addition of from about 0.01 to about 100 parts per million by weight of catalyst life extender relative to the weight of the total alkyl aromatic hydrocarbon in the feedstream 104, or from about 0.10 to about 10 parts per million, for example.

Just as the catalysts life extenders can be introduced into the dehydrogenation process by more that one method, it is also within the scope of the present invention to introduce the catalyst life extenders 106 to the dehydrogenation process at more than one rate. For example, the catalyst life extenders 106 can be introduced continuously or periodically, such as when catalyst activity levels fall below a predetermined level. In still another embodiment, the catalyst life extenders may be added at a relatively low level with additional catalyst life extender being added to the process when catalyst activity levels fall below a predetermined level. Accordingly, the system may include monitoring means (not shown) to monitor temperatures and chemical compositions to determine when conversion drops below a predetermined level.

Prior to the embodiments described herein, aqueous addition methods have been unsuccessful, at least in part because the feedstream 104 is usually passing at a very high velocity, such as 20 ft/s, or from about 10 ft/s to about 30 ft/s, or from about 15 ft/s to about 25 ft/s, or at a velocity of about 15 ft/s or more, for example, through a large diameter conduit, such as 54 inches to 60 inches.

Supply System

Surprisingly, the embodiments described herein are capable of adding catalyst life extenders to high temperature process streams while exhibiting minimal fouling/plugging of the either the reactors or process lines.

FIG. 3 illustrates a supply system 300. The supply system 300 is adapted to provide an aqueous catalyst life extender 106 to a first conduit 302 in which the feedstream (104a, 104b) is passing there through.

The supply system 300 generally includes a second conduit 304 adapted to provide the catalyst life extender 106 to the first conduit 302. The second conduit 304 is formed of a material compatible with high temperature processes, such as stainless steel, for example. The second conduit 304, may extend into the first conduit 302. For example, the second conduit 304 may be fitted through an aperture in the first conduit 302. In another embodiment, the second conduit 304 (shown in FIG. 3) is substantially flush with the first conduit 302. Further, the second conduit 304 is operably connected to the first conduit 302 so as to reduce shearing of the second conduit 304.

The catalyst life extender 106 is added to the first conduit 302 at a velocity sufficient to minimize fouling, which is also herein also referred to herein as a "sufficient linear velocity." As used herein, the term "velocity sufficient to minimize fouling" refers to a velocity such that any fouling experienced in the process lines and/or equipment does not have an unacceptable detrimental effect on the feedstream 104 flowing therethrough.

Various embodiments are described below that may be used alone or in combination with one another to provide the catalyst life extender 106 to the feedstream 104 at a sufficient linear velocity.

In one embodiment, the second conduit 304 has a small diameter. The "small diameter" is selected to provide either the sufficient linear velocity or may be selected to be used in combination with other embodiments to provide the sufficient linear velocity. For example, when the first conduit 302 has a diameter of from about 50 inches to about 65 inches, the second conduit 304 may have a diameter of about 0.1 inches, or less than about 0.25 inches, for example.

In another embodiment, a CLE gas 306 (e.g., a gas that is nonreactive with the catalyst life extender 106 or the feedstream 104) is supplied to the catalyst life extender 106 to increase the linear velocity of such. For example, the CLE gas 306 may be non-oxygen containing and may include fuel gas or nitrogen. As shown in FIG. 3, the CLE gas 306 may be premixed with or supplied to the second conduit 304 from a separate source. While the catalyst life extender 106 is generally an aqueous solution including from about 1 wt. % to about 50 wt. % catalyst life extender, the specific composition of the CLE 106 is determined by specific process parameters, such as the gas being used and the sufficient linear velocity. For example, a CLE water content of greater than about 50 wt. % may reduce the temperature of the gas 306, thereby reducing the actual linear velocity of the CLE 106.

FIG. 4 illustrates another embodiment wherein a supply system 400 includes a third conduit 402 formed around the perimeter of the second conduit 304. In such an embodiment, the second conduit may extend into the first conduit 302 (not shown), may be flush with an entrance into the first conduit 302 or may not extend to the entrance (not shown). Such placement may be used to overcome shearing of the second conduit 304 due to the high velocity of the feedstream 104 passing through the first conduit 302.

In one embodiment, the second conduit 304 may include a nozzle (not shown) to further aid the mixing of the CLE 106 with the feedstream 104. Such nozzle is adapted to minimize shearing and/or displacement due to the feedstream velocity.

In such an embodiment, the junction of the second conduit 304 and the third conduit 402 is sealed. As used herein, the term "fluid" refers to liquid or gas. The end of the third conduit 402 opposite the junction is open to the first conduit 302 and any fluid passing through the third conduit may also flow into the first conduit.

Further, this embodiment enables the on-line replacement of portions of the supply system should they experience an unacceptable amount of plugging. In such a situation, the tubing can be removed and replaced with an unfouled conduit without or minimizing costly shutdown time. The fouled conduit may be disposed of or cleaned for future use.

The supply system 400 may further include a gas supply 404 to cool the CLE 106. Such cooling gas 406 is generally adapted to prevent and/or minimize flashing of the CLE 106 upon contact with the feedstream 104. The cooling gas 406 may be the same gas as the CLE gas 306 or a different gas, but again is not reactive with the feedstream 104.

Although described herein in terms of catalytic dehydrogenation processes, the embodiments described herein may be used for aqueous salt addition into any high temperature conversion process, including the formation of gasoline fraction hydrocarbons from syntheses gas, dealkylation of alkylaromatics (e.g., toluene to benzene) and syntheses of ammonia from nitrogen and hydrogen. Generally, when referring to high temperature processes, the aqueous salt is added to a process stream having such high temperature.

EXAMPLES

Example 1

Via a system such as that illustrated in FIG. 4, wherein the diameter of the second conduit was 1 inch, a steam and ethylbenzene feedstream was contacted with a potassium promoted iron oxide dehydrogenation catalyst in a reaction to form styrene. The feedstream (10:1 molar ratio of steam: ethylbenzene) was fed to the reaction via a first conduit (54 inch diameter) at a temperature of about 1200° F. (649° C.) and a velocity of about 20 ft/s. Prior to the reactor inlet, aqueous potassium acetate was injected into the first conduit to contact and mix with the feed stream. The potassium acetate was at ambient temperature prior to injection.

After 2 months, a gamma scan was done of the first conduit, which revealed deposits near the junction of the first and second conduits.

Example 2

Via a system such as that illustrated in FIG. 4, wherein the diameter of the second conduit was ¼ inch, a steam and ethylbenzene feedstream was contacted with a potassium promoted iron oxide dehydrogenation catalyst in a reaction to form styrene. The feedstream (10:1 molar ratio of steam: ethylbenzene) was fed to the reaction via a first conduit (54 inch diameter) at a temperature of about 1200° F. (649° C.) and a velocity of about 20 ft/s. Prior to the reactor inlet, aqueous potassium acetate was injected into the first conduit to contact and mix with the feed stream. The potassium acetate was at ambient temperature prior to injection Two months after startup of the above process, a gamma scan of the conduit and the reactor observed essentially no deposits therein.

What is claimed is:

1. A method comprising providing a reaction vessel loaded with a dehydrogenation catalyst with a feedstream via a first conduit in operable communication with the reaction vessel, the feedstream comprising an alkyl aromatic hydrocarbon and the dehydrogenation catalyst adapted to convert the alkyl aromatic hydrocarbon to a vinyl aromatic hydrocarbon, and contacting the feedstream with an aqueous catalyst life extender comprising potassium acetate in the first conduit, wherein the aqueous catalyst life extender enters the first conduit via a second conduit having a diameter of less than about ¼ inches at a linear velocity sufficient to prevent vaporization of the catalyst life extender in the first conduit prior to contact with the feedstream, wherein the feedstream is passing through the first conduit at a velocity of greater than about 20 ft/s.

2. The method of claim 1, wherein the alkyl aromatic hydrocarbon comprises ethylbenzene and the vinyl aromatic hydrocarbon comprises styrene.

3. The method of claim 1, wherein the dehydrogenation catalyst comprises an iron compound and an alkali metal compound.

4. The method of claim 3, wherein the alkali metal compound comprises potassium.

5. The method of claim 1, further comprising supplying a gas to the aqueous catalyst life extender.

6. The method of claim 5, wherein the gas comprises a non oxygen containing gas.

* * * * *